(12) United States Patent
Miller et al.

(10) Patent No.: US 8,716,472 B2
(45) Date of Patent: May 6, 2014

(54) TRIPODAL CYCLOHEXANE DERIVATIVES AND THEIR USE AS CARBOHYDRATE RECEPTORS

(75) Inventors: Benjamin L. Miller, Penfield, NY (US); Prakash B. Palde, Rochester, NY (US); Peter C. Gareiss, Rochester, NY (US)

(73) Assignee: University of Rochester, Rochester, NY (US)

( * ) Notice: Subject to any disclaimer, the term of this patent is extended or adjusted under 35 U.S.C. 154(b) by 730 days.

(21) Appl. No.: 12/526,696

(22) PCT Filed: Oct. 16, 2007

(86) PCT No.: PCT/US2007/081533
§ 371 (c)(1),
(2), (4) Date: Aug. 11, 2009

(87) PCT Pub. No.: WO2008/048967
PCT Pub. Date: Apr. 24, 2008

(65) Prior Publication Data
US 2010/0041568 A1    Feb. 18, 2010

Related U.S. Application Data

(60) Provisional application No. 60/829,595, filed on Oct. 16, 2006.

(51) Int. Cl.
*C07D 401/14* (2006.01)
*C07D 403/14* (2006.01)
*C40B 30/04* (2006.01)
*C40B 40/10* (2006.01)
*C07K 5/06* (2006.01)
*C07K 5/08* (2006.01)
*C07K 5/10* (2006.01)
*C07K 7/06* (2006.01)
*C07H 17/02* (2006.01)

(52) U.S. Cl.
USPC ........... 544/180; 544/196; 544/197; 544/242; 544/323; 544/336; 546/255; 546/176; 546/263; 546/264; 436/87; 506/9; 506/18; 530/330; 530/331; 530/345; 536/17.3

(58) Field of Classification Search
USPC .......... 544/180, 196, 242, 323, 336; 546/255, 546/256, 176, 263, 264; 436/87; 506/9, 18; 530/330, 331, 345; 536/17.3
See application file for complete search history.

(56) References Cited

U.S. PATENT DOCUMENTS

| | | | |
|---|---|---|---|
| 3,528,988 A * | 9/1970 | Uelzmann | 546/255 |
| 3,646,041 A | 2/1972 | Uelzmann | |
| 4,477,616 A | 10/1984 | Minagawa et al. | |
| 6,140,041 A | 10/2000 | LaClair | |
| 6,903,101 B1 | 6/2005 | Dumas et al. | |
| 7,947,703 B2 * | 5/2011 | Parenty et al. | 514/285 |

FOREIGN PATENT DOCUMENTS

WO    WO 2005054241 A2 *    6/2005

OTHER PUBLICATIONS

Kubel-Pollak et al., New Journal of Chemistry (2006), 30(6), 851-860.*
Fan et al. J. Chem. Soc., Chem. Commun., 1251-1252, 1995.*
Raposo et al., Tetrahedron Letters (1995), 36(18), 3255-8.CAPLUS Abstract provided.*
Heilman et al. Journal of Macromolecular Science, Pure and Applied Chemistry (2003). CAPLUS Abstract provided.*
Chuang et al. Journal of the Chinese Chemical Society (Taipei, Taiwan) (2001), 48(2),193-200. CAPLUS Abstract provided.*
Matthew A. J. Duncton, Med. Chem. Commun., 2011, 2, 1135.*
Tajc et al., "A Designed Receptor for pH-Switchable Ion Binding in Water," JACS Communications 128:2532-33 (2006).

* cited by examiner

*Primary Examiner* — Venkataraman Balasubramanian
(74) *Attorney, Agent, or Firm* — LeclairRyan, a Professional Corporation

(57) ABSTRACT

A tri-podal compound according to formula (I) wherein, each Z is the same and is a substituted or unsubstituted N-heteroaromatic single-, multiple-, or fused-ring; and each A is the same, and can represent a direct bond between the cyclohexane ring and Z, or a carboxamide group (—C(O)—N(H)—). Use of the compounds in combinatorial libraries, methods of making the tripodal compounds, sensor devices for detecting carbohydrate targets, and methods of using the tripodal compounds to detect carbohydrate targets in a sample are also disclosed.

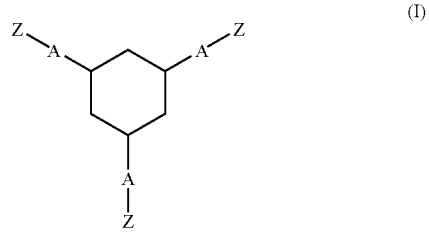

(I)

13 Claims, 9 Drawing Sheets

Scheme 1

Scheme 2

Scheme 3

| Heterocyclic Base (Z group; A= direct bond; $Y_n$ groups = H, $CH_3$, or $CO_2Et$) | Product | Compound | Isolated Yield (%) |
|---|---|---|---|
| pyridine | pyridine | Complex mixture | - |
| pyrazine | pyrazine | 2 | 28 |
| pyrimidine | pyrimidine | 3 | 26 |
| pyridazine | pyridazine | 4 | 5 |
| 1,3,5-triazine | 1,3,5-triazine | NR | - |
| ethyl isonicotinate | ethyl isonicotinate | 5 | 18 |
| ethyl nicotinate | ethyl nicotinate | 6 | 16 |
| quinoline | quinoline | Complex Mixture | - |
| 4-methylquinoline | 4-methylquinoline | 7 | 5 |
| benzoxazole | benzoxazole | NR | - |

Figure 4

Scheme 4

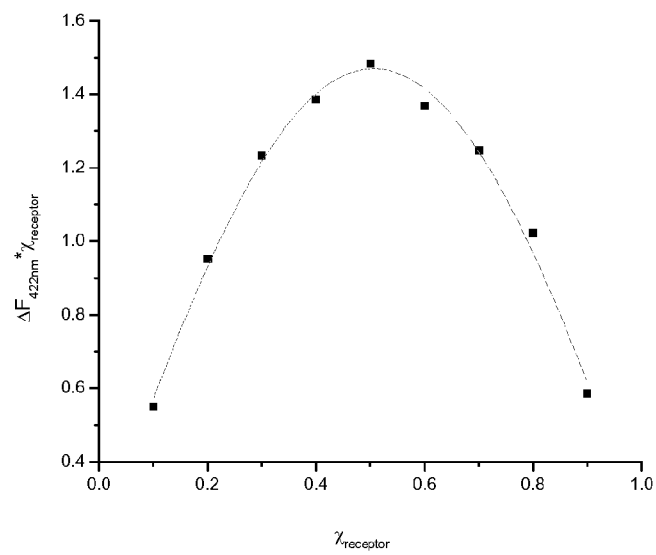
Figure 12
Figure 13A
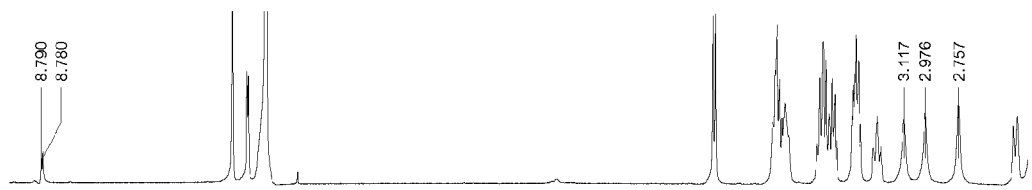
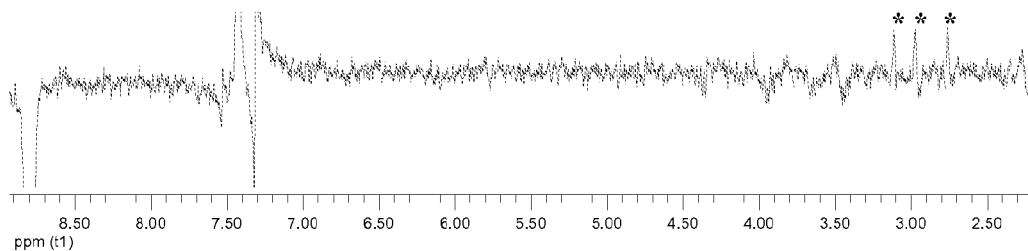
Figure 13B

TRIPODAL CYCLOHEXANE DERIVATIVES AND THEIR USE AS CARBOHYDRATE RECEPTORS

STATEMENT OF GOVERNMENT SPONSORSHIP

This invention was made with government support under grant number GM62825 awarded by the National Institutes of Health and grant number 2T32AR007472-16 awarded by the Department of Health and Human Services. The government has certain rights in the invention.

This application is a U.S. national stage application under 35 U.S.C. 371 of PCT Application No. PCT/US2007/081533, filed Oct. 16, 2007, which claims the priority benefit of U.S. Provisional Patent Application Ser. No. 60/829,595, filed Oct. 16, 2006, which is hereby incorporated by reference in its entirety.

BACKGROUND OF THE INVENTION

Carbohydrates represent a particularly enticing and important challenge to the understanding of molecular recognition (Davis et al., In Functional Synthetic Receptors, Schrader et al., eds., Wiley-VCH, Weinheim, p. 47 (2005)). In addition to their role in addressing the fundamental problem of understanding binding and selectivity, novel carbohydrate receptors have significant potential as tools in the rapidly evolving field of glycomics (Raman et al., Nature Meth. 2:817-824 (2005); Ratner et al., Chem. BioChem. 5:1375-1383 (2004)), as components of sensing systems for isolated sugars (Zhang et al., Org. Lett. 8:1649-1652 (2006); Gao et al., Tetrahedron 61:9111-9117 (2005); Yoon et al., J. Am. Chem. Soc. 114: 5874-5875 (1992); Shinkai et al., Biosens. Bioelectron. 20:1250-1259 (2004)) and for pathogens (Chan et al., J. Am. Chem. Soc. 123:11797-11798 (2001)), and as leads for the development of new therapeutic agents (Miller et al., J. Med. Chem. 48:2589-2599 (2005); Ding et al., J. Am. Chem. Soc. 126:13642-13648 (2004)). However, as has been noted by others, the design of organic receptors able to bind simple, non-ionic sugars via noncovalent interactions is a daunting task (Wiskur et al., Chem. Eur. J. 10:3792-3804 (2004)). This is particularly true when the goal is binding sugars in protonated solvents, since the solute looks much like ordered solvent.

A number of synthesis schemes have been described for various tri-podal receptors. These include a four-step process for the preparation of a tricatecholic-benzene receptor for carbohydrates (i.e., from 1,3,5-triethylbenzene and pyrogallol) (Cacciarini et al., J. Org. Chem., 72(10):3933-3936 (2007); a multi-step process for preparation of the tri-imidazolinyl-benzene tri-podal receptors (i.e., preparation of intermediate 1-aminomethyl-2,4,6-triethyl-3,5-(N-(imidazoline-2-yl-aminomethyl)benzene from 2,4,6-triethyl-1,3,5-tri (aminomethyl)benzene, and then reaction of the intermediate with (2-formylphenyl)boronic acid followed by reduction) (Lavigne et al., Angew. Chem. Int. Ed. 38:3666-3669 (1999)); and a multi-step process for the formation of tri-pyrazolyl benzene tri-podal receptors (i.e., via reaction of the sodium anion of 3,5-dimethyl pyrazole with 1,3,5-tris(bromomethyl)-2,4,6-triethylbenzene) (Chin et al., Angew. Chem. Int. Ed. 38:2756-2759 (1999)). For tri-podal receptors lacking the benzene core, such as the tyrosine-based receptor described in Tajc et al., J. Am. Chem. Soc. 128:2532-2533 (2006), a multi-step process is described for the reduction of cyclohexane 1,3,5-tricarboxylic acid to the trimethanol intermediate, and reaction of the trimethanol intermediate with N-Boc (or N-Fmoc) tyrosine under standard coupling conditions, followed by deprotection.

It would be desirable to identify a simpler synthesis scheme that can be used to develop novel tripodal receptors, which can then be used for carbohydrate and other macromolecular recognition.

Tripodal receptors have been a mainstay of the molecular recognition field (Lavigne et al., Angew. Chem. Int. Ed. 38:3666-3669 (1999); Chin et al., Angew. Chem. Int. Ed. 38:2756-2759 (1999)). In the realm of noncovalent carbohydrate recognition, tripodal receptors based on arenes have been explored extensively by the Mazik group, who demonstrated that aromatic compounds incorporating aminopyridine side chains (Mazik et al., Angew. Chem. Int. Ed. 39:551-554 (2000)) are able to bind alkylpyranosides as 1:1 and 2:1 complexes in chloroform with substantial affinity and selectivity (Mazik et al., Org. Lett. 8:855-858 (2006)). Other notable examples of arene-based tripodal carbohydrate receptors have been described by the Roelens (Vacca et al., J. Am. Chem. Soc. 126:16456-16465 (2004)), Abe (Abe et al., Org. Lett. 7:59-61 (2005)), and Schmuck (Schmuck et al., Org. Lett. 7:3517-3520 (2005)) groups, who studied hexasubstituted benzene-based tripodal receptors incorporating urea, phenol, and guanidinium substituents, respectively. Despite these major achievements, and elegant structures such as the carbohydrate-binding cage structure developed by Davis and coworkers (Velasco et al., Org. Biomol. Chem. 2:645-647 (2004)), binding in protic solvent remains an essentially unsolved problem.

Several of the present inventors demonstrated prior success with the use of a cycloalkane oligomer as a conformational control element in the development of receptors for lipid A (Hubbard et al., J. Am. Chem. Soc. 123:5810-5811 (2001); Gareiss et al., Eur. J. Org. Chem. 53 (2007)). While highly substituted cyclohexanes, for example Kemp's Triacid, have proven useful as components in molecular recognition systems (Kocis et al., Tetrahedron Lett. 36:6623-6626 (1995); Rebek et al., J. Am. Chem. Soc. 109:2426-2431 (1987); Kemp et al., J. Org. Chem. 46:5140-5143 (1981)), receptors based on a simple cis-1,3,5-trisubstituted cyclohexane core are less well known (Tajc et al., J. Am. Chem. Soc. 128:2532-2533 (2006); Ryu et al., Bull Kor. Chem. Soc. 22:1293-1294 (2001)).

The present invention is directed to overcoming these and other deficiencies in the art.

SUMMARY OF THE INVENTION

A first aspect of the present invention relates to a compound according to formula (I)

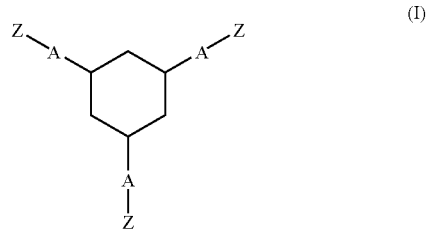

wherein each Z is the same and is a substituted or unsubstituted N-heteroaromatic ring or ring system; and each A is the same, and can represent a direct bond between the cyclohexane ring and Z, or a carboxamide group (—C(O)—N(H)—).

A second aspect of the present invention relates to a method of making a compound according the first aspect of the present invention. The method includes reacting 1,3,5-tricarboxylic acid cyclohexane with a substituted or unsubstituted N-heteroaromatic ring (H—Z) or amine-derivative thereof (NH$_2$—Z) under conditions effective to form the compound according to formula (I). Preferred routes of synthesis include a single-step tri-directional Minisci reaction to afford compounds where A is a direct bond, and an amidation reaction to afford compounds where A is a carboxamide linker group.

A third aspect of the present invention relates to a compound according to formula (II) that is derived from the compound according to formula (I). The compound according to formula (II) is shown below:

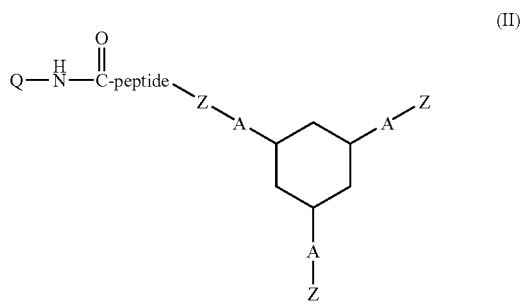

(II)

wherein, each -A-Z group is defined as in formula (I);

the peptide comprises 2 to 5 amino acids, and at least one of the amino acids is capable of forming a disulfide bond, sulfinyl linkage, or olefin bond; and Q is either H, a substrate, or a detection label.

According to one embodiment, two or more compounds of formula (II) are linked together via di-sulfide bond, sulfinyl linkage, or olefin bond, and Q is a substrate for one compound and H or a detection label for the other compound.

A fourth aspect of the present invention relates to a detector chip that includes a substrate and a compound according to the first aspect of the present invention that is bound to the substrate. The compound can be present in the form of a monomer of formula (I) or (II), or a dimer formed of two monomers according to formula (II). The dimers are particularly desirable when presented in a combinatorial library, having one monomer bound to a substrate (Q=substrate) and the other monomer having Q=H or the detectable label.

A fifth aspect of the present invention relates to a detector device that includes the detector chip according to the fourth aspect of the present invention and a detector that detects the presence of a carbohydrate bound to the compound.

A sixth aspect of the present invention relates to a method of detecting the presence of a carbohydrate in a sample. This method includes the steps of: providing a sample that may contain a carbohydrate of interest; exposing the sample to a compound according to the first aspect of the present invention; and determining whether the compound binds to the carbohydrate of interest. The compound can be present in the form of a monomer of formula (I) or (II), or a dimer formed of two monomers according to formula (II). In addition, the compound can be present in solution or tethered to a substrate (i.e., a detector chip of the present invention).

These compounds of formula (I) have several of the characteristics that are important for carbohydrate receptors: a conformationally constrained (but not necessarily completely rigid) core, and coupled with heteroatom functionality able to participate in hydrogen bonding and electrostatic interactions. A tri-directional Minisci reaction has been used to prepare a number of the tripodal compounds. In the accompanying examples, several receptors are demonstrated efficiently to bind monosaccharides in both protonated and non-protonated solvents.

BRIEF DESCRIPTION OF THE DRAWINGS

FIG. 4 is a chart illustrating the substituted or unsubstituted N-heterocycle and the resulting compound (Compounds 2-7), along with its yield.

FIG. 5A is part of $^1$H NMR spectra of Compound 11 (CDCl$_3$, 298° K) showing the aromatic and amide proton resonances after addition of (bottom to top) 0, 0.2, 0.4, 0.6, 0.8, 1.0, 1.2, 1.4, 1.6, 1.8, and 2.0 equivalents of n-octyl-β-D-glucopyranoside. FIG. 5B is a graph showing the binding isotherm between Compound 11 and n-octyl-β-D-glucopyranoside.

FIG. 9A shows part of $^1$H NMR spectra (CDCl$_3$, 298° K) of n-octyl-β-D-glucpyranoside (3,4 and 2-OH proton resonances from left to right) after addition of (bottom to top) 0, 0.17, 0.35, 0.52, 0.86, 1.20, 1.59, 2.40, 3.20, 3.60 and 4.80 equivalents of Compound 12. FIG. 9B shows a Jobs plot illustrating 1:1 stoichiometry of the complex between Compound 12 and n-octyl-β-D-glucopyranoside.

FIG. 11A shows fluorescence excitation and emission spectra of Compound 7 in methanol. FIG. 11B shows the increase in the fluorescence intensity of Compound 7 upon addition of increasing amount of n-octyl-α-D-glucopyranoside in methanol. FIG. 11C is the binding isotherm for the interaction between Compound 7 and n-octyl-α-D-glucopyranoside.

FIG. 12 is a Job plot for the complex formed between Compound 7 and n-octyl-α-D-glucopyranoside. The plot illustrates a 1:1 binding stoichiometry.

FIGS. 13A-B illustrate NMR and NOE spectral analysis of Compound 12. FIG. 13A is the 1D NMR spectrum of Compound 12 [1 mM] complexed with n-octyl-β-D-glucpyranoside [3 mM]. The irradiated frequency corresponding to C-6 ArH on pyridines of Compound 12 (δppm=8.985) is marked. The 3, 2 and 4-OH groups (left to right) of the sugar are also marked. FIG. 13B is a 1D difference NOE spectrum showing a strong positive intramolecular NOE to C-5 ArH and weak positive intermolecular NOE's (marked by the *) to the 3, 2 and 4-OH groups of the sugar from the irradiated proton (C-6 ArH of pyridine rings).

DETAILED DESCRIPTION OF THE INVENTION

The present invention relates to tripodal compounds having a cyclohexane core structure, combinatorial libraries containing the same, methods of making the tripodal compounds, sensor chips and devices for detecting carbohydrate targets, and methods of using the tripodal compounds to detect carbohydrate targets in a sample.

Preferred tripodal compounds of the invention have a structure according to formula (I)

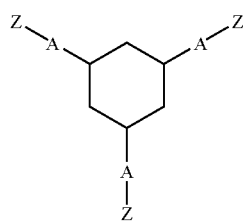

(I)

wherein,
each Z is the same and is a substituted or unsubstituted N-heteroaromatic ring; and
each A is the same, and can represent a direct bond between the cyclohexane ring and Z, or a carboxamide group (—C(O)—N(H)—).

Figure 2:
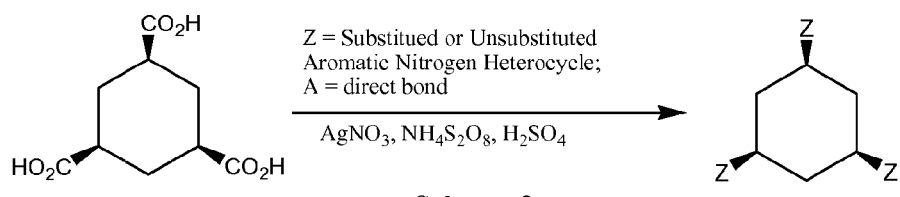
FIG. 2 shows Scheme 2, which is a tridirectional Minisci reaction performed in accordance with one embodiment of the present invention.
Figure 7:
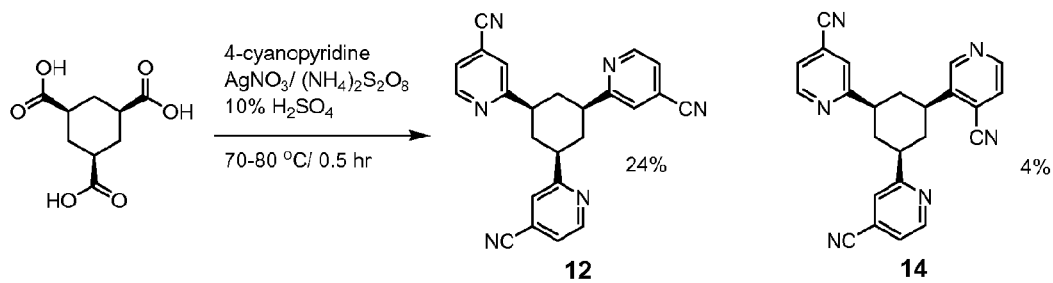
FIG. 7 shows Scheme 4, which is a tridirectional Minisci reaction using 4-cyanopyridine as the N-heterocycle. The major product (Compound 12) and minor product (Compound 14) and their respective yields are shown.

Preferably, the compounds of formula (I) are characterized by a cis structural arrangement of the three identical -A-Z groups. Given the nature of the tri-directional Minisci reaction described in greater detail hereinafter (all stereochemistry is lost by the reaction intermediates), this can be achieved regardless of using cis-1,3,5-tricarboxylic acid cyclohexane as the starting material. See FIGS. 2, 3, and 7 (Schemes 2-4).

Positional isomers are also encompassed by the present invention. Although most preferred compounds possess N-heteroaromatic rings that bind to the cyclohexane core (either directly or via the A group) at only the 2-position (i.e., 2,2',2" configurations) or only the 4-position (i.e., 4,4',4" configurations), positional isomers containing 2,2',3' configurations and 4,4',6" configurations have also been obtained.

The substituted or unsubstituted N-heteroaromatic ring can be any single- multiple-, or fused-ring N-heteroaromatic.

Exemplary unsubstituted N-heteroaromatic rings include, without limitation, pyridines, pyrazines, pyrimidines, pyridazines, pyrazoles, indazoles, pyrroles, indoles, isoindoles, imidazoles, benzimidazoles, purines, quinolines, isoquinolines, quinoxalines, quinazolines, cinnolines, acridines, and triazines. In addition, the N-heteroaromatic rings can also include additional O- or S-hetero atoms, such as oxazoles, benzoxazoles, isooxazoles, benzisooxazoles, thiazoles, and benzothiazoles.

The substituted N-heteroaromatic rings can include one or more substituents bonded at various positions to the one or more ring structures. Depending on the number of ring nitrogens, substituted single-ring N-heteroaromatics can contain from one up to four substituents, which can be the same or different. For example, substituted pyridine rings can contain up to four substituents, whereas pyrimidines and pyridazines can contain up to three substituents. Likewise, multiple- or fused-ring N-heteroaromatics can contain from one up to six substituents, which can be the same or different. For example, quinolines and isoquinolines can contain up to six substituents, whereas quinoxalines, quinazolines, and cinnolines can contain up to five substituents.

Suitable substituents, generically designated $Y_n$ ($Y_1$, $Y_2$, etc.), include, without limitation, —COO—$R_1$ where each $R_1$ is independently —H or a C1 to C18 hydrocarbon that is saturated or unsaturated; -(hydrocarbon)$_n$-$R_2$ where the hydrocarbon is saturated or unsaturated, n is an integer from 0 to 20, and each $R_2$ is independently —OH, —CH₃, —COOH, —NH₂; —O-(hydrocarbon)$_m$$R_3$ where the hydrocarbon is saturated or unsaturated, m is an integer from 0 to 20, and each $R_3$ is independently —OH, —CH₃, —COOH, —NH₂; —CN; —NR₄R₅ where each of R₄ and R₅ is independently H, methyl, ethyl, or propyl; —N(H)-(hydrocarbon)$_p$R₆ where the hydrocarbon is saturated or unsaturated, p is an integer from 0 to 20, and R₆ is —OH, —CH₃, or a second N-heteroaromatic ring selected from the group of pyridinyl, pyrazinyl, pyrimidinyl, triazinyl, pyridazinyl, imidazolyl, quinolyl, quinazolyl, benzoxazolyl, benzimidazolyl, and benzothiazyl.

Thus, the substituted Z group (N-heteroaromatic ring or rings) can be represented as the structures IIIa (single ring) or IIIb or IIIc (multi-ring) shown below:

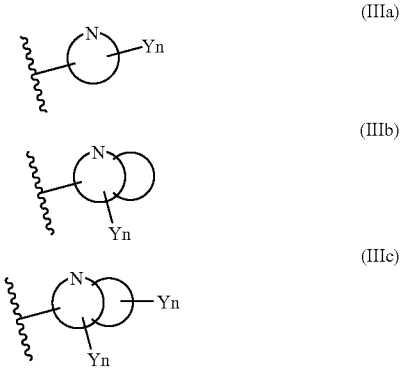

It should be appreciated that multi-ring structures and fused-ring structures may contain more than two rings. The generic structures of formula IIIb or IIIc are merely exemplary.

Exemplary substituted Z groups include, without limitation, 4-cyanopyridine, 4-alkyl(C1 to C4)pyridines, 4-alkoxy (C1 to C4)pyridines, 4-alkyl(C1 to C4)ester pyridines (e.g., isonicotinates), 3-alkyl(C1 to C4)ester pyridines (e.g., nicotinates), 4-carboxylic acid pyridines, 4-alkyl(C1 to C4)-2-acetamido pyridines, 4-amino pyridines, 4-cyano-6-(hydroxyalkyl(C1 to C4)amino)pyridines, 4-cyano-6-(N-(pyridin-2-ylalkyl(C1 to C4))amino)pyridines, 3,5-alkoxy (C1 to C4)-4-cyano-6-(hydroxyalkyl(C1 to C4)amino) pyridines, 3,5-alkoxy(C1 to C4)-4-cyano-6-(N-(pyridin-2-ylalkyl(C1 to C4)amino)pyridines, 4-carboxylic acid-6-(hydroxyalkyl(C1 to C4)amino)pyridines, 4-carboxylic acid-6-(N-(pyridin-2-ylalkyl(C1 to C4)amino)pyridines, 4-alkyl (C1 to C4)-6-(hydroxyalkyl(C1 to C4)amino)pyridines, 4-alkyl(C1 to C4)-6-(N-(pyridin-2-ylalkyl(C1 to C4))amino) pyridines, 4-alkoxy(C1 to C4)-6-(hydroxyalkyl(C1 to C4)amino)pyridines, 4-alkoxy(C1 to C4)-6-(N-(pyridin-2-ylalkyl(C1 to C4)amino)pyridines, 4-amino-6-(hydroxyalkyl (C1 to C4)amino)pyridines, 4-amino-6-(N-(pyridin-2-ylalkyl(C1 to C4))amino)pyridines, 4-alkyl(C1 to C4)quinolines, 4-cyanoquinoline, 4-alkoxy(C1 to C4)quinolines, 4-alkyl(C1 to C4)ester quinolines, 4-alkylamino(C1 to C4)quinolines, 6-cyanoquinoline, 6-alkyl(C1 to C4)quinolines, 6-alkoxy(C1 to C4)quinolines, 6-alkyl(C1 to C4)ester quinolines, 6-alkylamino(C1 to C4)quinolines, 5-cyanopyrazine, 5-alkyl(C1 to C4)pyrazines, 5-alkoxy(C1 to C4)pyrazines, 5-alkyl(C1 to C4)ester pyrazines, 5-alkylamino(C1 to C4)pyrazines, 6-cyanopyrazine, 6-alkyl(C1 to C4)pyrazines, 6-alkoxy(C1 to C4)pyrazines, 6-alkyl(C1 to C4)ester pyrazines, 6-alkylamino(C1 to C4)pyrazines, 5,6-alkyl(C1 to C4)pyrazines, 5,6-alkoxy(C1 to C4)pyrazines, 5,6-alkylamino(C1 to C4)pyrazines, 5-cyanopyrimidine, 5-alkyl(C1 to C4)pyrimidines, 5-alkoxy(C1 to C4)pyrimidines, 5-alkyl (C1 to C4)ester pyrimidines, 5-alkylamino(C1 to C4)pyrimidines, 2-cyanopyrimidine, 2-alkyl(C1 to C4)pyrimidines, 2-alkoxy(C1 to C4)pyrimidines, 2-alkyl(C1 to C4)ester pyrimidines, 2-alkylamino(C1 to C4)pyrimidines, 2,5-alkyl(C1 to C4)pyrimidines, 2,5-alkoxy(C1 to C4)pyrimidines, 2,5-alkylamino(C1 to C4)pyrimidines, 6-cyanopyridazine, 6-alkyl(C1 to C4)pyridazines, 6-alkoxy(C1 to C4)pyridazines, 6-alkyl(C1 to C4)ester pyridazines, 6-alkylamino (C1 to C4)pyridazines, 6-cyanoquinoxaline, 6-alkyl(C1 to C4)quinoxalines, 6-alkoxy(C1 to C4)quinoxalines, 6-alkyl (C1 to C4)ester quinoxalines, 6-alkylamino(C1 to C4)quinoxalines, 6-cyanoquinazoline, 6-alkyl(C1 to C4)quinazolines, 6-alkoxy(C1 to C4)quinazolines, 6-alkyl(C1 to C4)ester quinazolines, 6-alkylamino(C1 to C4)quinazolines, 2-cyanoquinazoline, 2-alkyl(C1 to C4)quinazolines, 2-alkoxy(C1 to C4)quinazolines, 2-alkyl(C1 to C4)ester quinazolines, and 2-alkylamino(C1 to C4)quinazolines.

Exemplary compounds of the present invention include, without limitation,
1,3,5-tris-pyrazin-2-yl cyclohexane (Compound 2);
1,3,5-tris-pyrimidin-2-yl cyclohexane (Compound 3);
1,3,5-tris[1,3,5-triazin-2-yl]cyclohexane;
1,3,5-tris-pyridazin-3-yl cyclohexane (Compound 4);
1,3,5-tris-imidazol-2-yl cyclohexane;
1,3,5-tris-pyridin-2-yl cyclohexane;
1,3,5-tris-(4-cyano)pyridin-2-yl cyclohexane (Compound 12);
1,3,5-tris-(4-carboxylic acid)pyridin-2-yl cyclohexane;
1,3,5-tris-(4-ethyl ester)pyridin-2-yl cyclohexane (Compound 5);
1,3,5-tris-(3-ethyl ester)pyridin-2-yl cyclohexane (Compound 6);
1,3,5-tris-(4-ethyl-2-acetamido)pyridin-2-yl cyclohexane;
1,3,5-tris-(4-methyl)pyridin-2-yl cyclohexane;
1,3,5-tris-(4-methoxy)pyridin-2-yl cyclohexane;
1,3,5-tris-(4-amino)pyridin-2-yl cyclohexane;
1,3,5-tris-(4-cyano-6-(2-hydroxyethylamino))pyridin-2-yl cyclohexane;
1,3,5-tris-(4-cyano-6-(3-hydroxypropylamino))pyridin-2-yl cyclohexane;
1,3,5-tris-(4-cyano-6-(N-(pyridin-2-ylmethyl)amino)-pyridin-2-yl cyclohexane;
1,3,5-tris-(3,5-methoxy-4-cyano-6-(2-hydroxyethylamino)) pyridin-2-yl cyclohexane;
1,3,5-tris-(3,5-methoxy-4-cyano-6-(3-hydroxypropylamino))pyridin-2-yl cyclohexane;
1,3,5-tris-(3,5-methoxy-4-cyano-6-(N-(pyridin-2-ylmethyl) amino)-pyridin-2-yl cyclohexane;
1,3,5-tris-(4-carboxylic acid-6-(2-hydroxyethylamino))pyridin-2-yl cyclohexane;
1,3,5-tris-(4-carboxylic acid-6-(3-hydroxypropylamino))pyridin-2-yl cyclohexane;
1,3,5-tris-(4-carboxylic acid-6-(N-(pyridin-2-ylmethyl) amino)-pyridin-2-yl cyclohexane;
1,3,5-tris-(4-methyl-6-(2-hydroxyethylamino))pyridin-2-yl cyclohexane;
1,3,5-tris-(4-methyl-6-(3-hydroxypropylamino))pyridin-2-yl cyclohexane;
1,3,5-tris-(4-methyl-6-(N-(pyridin-2-ylmethyl)amino)-pyridin-2-yl cyclohexane;
1,3,5-tris-(4-methoxy-6-(2-hydroxyethylamino))pyridin-2-yl cyclohexane;
1,3,5-tris-(4-methoxy-6-(3-hydroxypropylamino))pyridin-2-yl cyclohexane;
1,3,5-tris-(4-methoxy-6-(N-(pyridin-2-ylmethyl)amino)-pyridin-2-yl cyclohexane;
1,3,5-tris-(4-amino-6-(2-hydroxyethylamino))pyridin-2-yl cyclohexane;
1,3,5-tris-(4-amino-6-(3-hydroxypropylamino))pyridin-2-yl cyclohexane;
1,3,5-tris-(4-amino-6-(N-(pyridin-2-ylmethyl)amino)-pyridin-2-yl cyclohexane;
1,3,5-tris-(4-methylquinolin-2-yl)cyclohexane (Compound 7); and
1,3,5-tris(6-methylpyridin-2-yl)cyclohexane-1,3,5-tricarboxamide (Compound 11).

The compounds of the present invention can be prepared by reacting 1,3,5-tricarboxylic acid cyclohexane with a substituted or unsubstituted N-heteroaromatic single-, multiple-, or fused-ring reactant H—Z under conditions effective to undergo protonation and thereby form the compound according to formula (I). As noted above, the 1,3,5-tricarboxylic acid cyclohexane need not be a substantially pure cis stereoisomer, because the stereochemistry is lost in the intermediate radical and the substantially pure cis stereoisomer is the strongly favored product.

Figure 1:
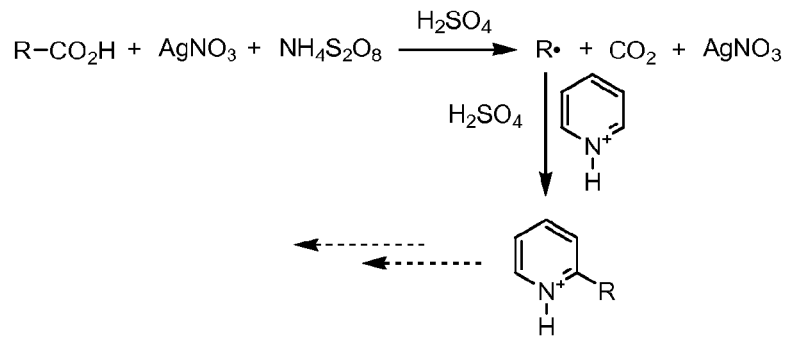
FIG. 1 shows Scheme 1, which is the prior art Minisci reaction as previously described (Minisci et al., *Tetrahedron* 27:3575-3579 (1971), which is hereby incorporated by reference in its entirety).

The synthesis procedure is basically carried out using the known Minisci reaction conditions, except that the reaction is carried out in a tri-directional manner given use of the 1,3,5-tricarboxylic acid cyclohexane as a starting material. As shown in FIG. 1, the prior art Minisci reaction is illustrated as Scheme 1. First reported in 1971, the Minisci reaction provides rapid entry into substituted heterocycles via addition of an alkyl radical generated by silver-catalyzed oxidative decarboxylation (Scheme 1) to a protonated aromatic base (Minisci et al., *Tetrahedron* 27:3575-3579 (1971), which is hereby incorporated by reference in its entirety). Because the reaction is simple, generally regioselective, and suitable for a wide range of alkyl and acyl radicals (Fontana et al., *J. Org. Chem.* 56:2866-2869 (1991); Bennasar et al., *J. Org. Lett.* 3:1697-1700 (2001), each of which is hereby incorporated by reference in its entirety), it has found broad usage in the synthesis of functionalized heterocycles, in recent years including products as diverse as quinolines intended as anti-tuberculosis agents (Jain et al., *Bioorg. Med. Chem. Lett.*

13:1051-1054 (2003); Vangapandu et al., *Bioorg. Med. Chem.* 12:2501-2508 (2004); Vaitilingam et al., *Bioorg. Med. Chem.* 12:4179-4188 (2004), each of which is hereby incorporated by reference in its entirety), and N-alkyl 1,2,4-triazoles (Hansen et al., *Tetrahedron Lett.* 42:7353-7355 (2001), which is hereby incorporated by reference in its entirety). In many respects, the reaction is complementary to other methods for the production of carbon-centered radicals from carboxylic acids, including the Barton decarboxylation (Barton et al., *J. Chem. Soc. Chem. Commun.* 939 (1983), which is hereby incorporated by reference in its entirety). It is believed that the Minisci reaction has not been used previously in a bi- or tri-directional process.

Alternatively, compounds having the carboxamide linking group (A) can be formed via reaction between cis-1,3,5-cyclohexane tricarboxylic acid and $NH_2$—Z (amino-derived N-heterocycle). Briefly, anhydrous N,N-dimethylformamide can be added to a slurry of cis-1,3,5-cyclohexane tricarboxylic acid and thionyl chloride in anhydrous $CH_2Cl_2$, and the mixture can then be allowed to reflux and afterward dried in vacuo. An aliquot of the triacid chloride diluted in $CH_2Cl_2$ is then combined with the amino-derived N-heterocycle, and after sufficient duration (e.g., 24 hours) the resulting solution with precipitate can be treated with water and dried in vacuo to recover the tri-podal compound having the carboxamide linking group.

Another aspect of the invention relates to a combinatorial library, described hereinafter, that utilizes intermolecular bridges between compounds according to formula (II) to afford a dimeric structure. Formula (II) is shown below.

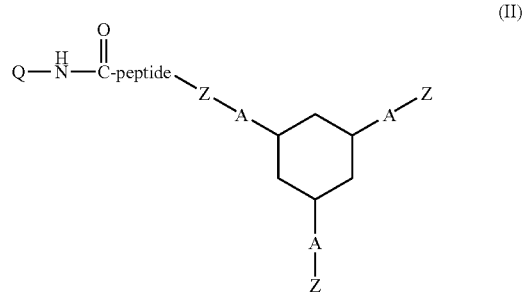

(II)

wherein, each -A-Z group is defined as in formula (I) above; the peptide preferably comprises 2 to 5 amino acids and at least one of the amino acids is capable of forming a disulfide bond, sulfinyl linkage, or olefin bond (with another amino acid residue in the peptide sequence of another compound of formula II); and Q is either H, a substrate, or a detection label (e.g., a fluorophore).

Compounds of formula II can be prepared by modifying the compounds according to formula I through standard peptide-coupling reaction with the intermediate Q-N(H)—C(O)-peptide.

In the peptide group, the amino acid that is capable of forming a disulfide bond, sulfinyl linkage, or olefin bond is present at any position in the peptide sequence. Formation of disulfide bonds, sulfinyl linkages, and olefin bonds is well known in the art. Disulfide bonds are formed by a covalent coupling of thiol groups from a cysteine or cysteine derivative. Sulfinyl linkages can be formed by well-known procedures, either by oxidation of a disulfide bond with mCPBA (Chayajarus et al., *Tetrahedron Lett.* 47:3517-3520 (2006), which is hereby incorporated by reference in its entirety) or by oxidation with dimethyl dioxirane (Bourles et al., *Angew.* *Chem. Int. Ed.* 44:6162-6165 (2005), which is hereby incorporated by reference in its entirety). Olefin bonds can be formed by α-amino acids having an unsaturated hydrocarbon sidechain using known procedures, such as those disclosed in PCT Patent Application Publication No. WO 2004/101476, which is hereby incorporated by reference in its entirety.

In a preferred embodiment, the peptide is a dipeptide, tripeptide, or tetrapeptide, and the amino acid capable of forming a disulfide bond, sulfinyl thio linkage, or olefin bond can be any one of the two to four residues.

Any combination of amino acids can be used in the compounds of formula (II), including without limitation L-amino acids, D-amino acids, and N-methyl amino acids.

Inert substrates (Q) include, without limitation, resins, glass, thermoplastics, polymer materials, semiconductor materials, and metals. Suitable resins include, without limitation, polystyrene, polystyrene-co-divinylbenzene, and polyethylene glycol/polystyrene-co-divinylbenzene graft polymers. Suitable metals include, without limitation, gold, silver, and platinum. Suitable semiconductor materials include, without limitation, silicon, germanium, doped-silicon alloys, and compound materials such as gallium arsenide and indium phosphide.

In a preferred embodiment, the inert substrate is a resin bead having a diameter of between about 150 μm to about 250 μm.

The two compounds of formula (II) that are linked together can be the same or different. Preferably, even when the two compounds are substantially the same, one compound includes a Q moiety that is a substrate and the other includes a Q moiety that is either H or a detection label.

A further aspect of the present invention relates to sensor chips and detector devices that can be used to identify a carbohydrate target in a sample. The sensor chip, in the broadest sense, is a substrate (whether a planar surface or a particle surface) that has covalently or noncovalently bound thereon a compound of the present invention. The substrate can also be in the form of an array that includes a plurality of discrete locations on the surface of a chip, with one compound of a particular type being bound to each discrete site. Thus, the array can be used collectively to bind multiple carbohydrate targets. Detector devices will contain an appropriate sensor mechanism to detect a change in a property of the sensor as a result of the compound binding to a target carbohydrate. The detector device can be any suitable detector, preferably one that operates by interferometry, reflectance spectrum shift, luminescence spectrum shift, arrayed imaging reflectometry, fluorescence spectrum intensity enhancement or quenching, UV-Vis spectrum intensity enhancement or quenching, or mass spectrometry.

Suitable sensor devices for use in the present invention include, without limitation, calorimetric nanocrystal sensors of the type disclosed in PCT International Application No. PCT/US02/18760 to Miller et al., filed Jun. 13, 2002 which is hereby incorporated by reference in its entirety; microcavity biosensors of the type disclosed in PCT International Application No. PCT/US02/05533 to Chan et al., filed Feb. 21, 2002, which is hereby incorporated by reference in its entirety; and reflective interferometric sensors of the type disclosed in PCT International Application No. PCT/US02/34508 to Miller et al., filed Oct. 28, 2002, which is hereby incorporated by reference in its entirety. Other sensor devices can include mass spectrometers and UV spectral analyzers.

Basically, the sensor devices can be used to detect the presence of a target carbohydrate in a sample. This can be carried out by providing a sample that may contain a carbohydrate of interest; exposing the sample to a compound of the present invention (i.e., as presented in a sensor device); and then determining whether the compound binds to the carbohydrate of interest. The actual detection can be carried out by the above-listed means, or any other suitable means.

As demonstrated in the examples, the carbohydrate of interest can include α- or β-alkyl glucopyranosides, α- or β-alkyl galactopyranosides, and α- or β-alkyl mannopyranosides. Moreover, these carbohydrates can be detected in either protic organic solvents (such as methanol, ethanol, isopropyl alcohol, etc.) or non-polar organic solvents (such as chloroform, other hydrocarbons, etc.). Sensor chips created from collections of these molecules will have utility for the detection of tumor antigens (TN-antigen), sialic acid, blood group antigens, mucins, and various glycosylated proteins.

EXAMPLES

The following examples are intended to illustrate the present invention, but are not intended to limit the scope of the appended claims.

Example 1

Procedure for Tri-Directional Radical Alkylation (Minisci-Type) Reaction

The results demonstrated below are believed to represent the first success in preparing tri-podal compounds using a tridirectional Minisci-type radical alkylation reaction. Because this procedure provides functional organic molecules in a single step, it fulfills many criteria of an ideal synthesis.

To a solution of 1,3,5-cyclohexane tricarboxylic acid (1 mmol) in 10% $H_2SO_4$ (5 ml) was added silver nitrate (0.6 mmol) and the N-heterocycle (10 mmol). The reaction mixture was heated to 80° C. A saturated solution of ammonium persulfate (10 mmol) in water was added dropwise over 10 minutes to the reaction mixture with evolution of carbon dioxide (indicated by bubbling in the solution). After emission of carbon dioxide ceased, the reaction mixture was allowed to stir for an additional 20 min at 80° C. The reaction mixture was then poured into ice and neutralized using saturated ammonium hydroxide solution (q.s). The resulting suspension was extracted with chloroform and the organic extract was washed with brine solution. Finally, the organic layer was dried over $Na_2SO_4$ and concentrated to yield crude product. The crude product was then purified using flash chromatography (appropriate proportions of methanol and dichloromethane).

Initial trials employing pyridine (FIG. 4) as the radical acceptor and cis-1,3,5-cyclohexanetricarboxylic acid reacted under modified Minisci conditions (1.0 eq. triacid, 0.6 eq. $AgNO_3$, 10 eq. $NH_4S_2O_8$, 10 eq. heterocyclic base, excess $H_2SO_4$) produced inseparable mixtures of regioisomeric products. Since both the pyridine 2- and 4-positions are available for reaction with the intermediate secondary radical, this outcome was not altogether surprising. In contrast, reaction with pyrazine under analogous conditions produced the desired (2,2',2")trisubstituted compound 2 in 24% isolated yield as the major product (FIG. 4). Yield of the major product was strongly dependent on the use of an excess of heterocyclic base in the reaction, and one could envision further improvements by employing an even larger amount. However, difficulty with separating unreacted starting material as well as the expense of the reagent itself must be balanced against the desire to optimize yields, and it was discovered that a 10-fold excess represented a reasonable compromise.

The scope of this reaction was then examined by varying the identity of the heterocyclic base while keeping the radical source constant. As shown in FIG. 4, yields of major products were remarkably consistent for reaction with pyrimidine (affording Compound 3), ethyl isonicotinate (affording Compound 5), and ethyl nicotinate (affording Compound 6). In contrast, reaction with pyridazine (affording Compound 4) produced only a 5% yield of the desired product. No reaction was observed with triazine or benzoxazole. Like pyridine, reaction with quinoline produced only a complex mixture of inseparable products.

Compound 7 was synthesized because it was expected that this compound would allow monitoring of carbohydrate binding by fluorescence spectroscopy (the quinoline moiety is a known fluorophore). The synthesis was effected in a similar way as that of Compound 12, where cis-cyclohexane 1,3,5-tricarboxylic acid was reacted with 4-methylquinoline in a tri-directional Minisci reaction to obtain Compound 7 in 5% yield. Studies by Minisci and coworkers demonstrated that radical alkylation of lepidine proceeds more rapidly in nonpolar solvent (Minisci et al., *J. Org. Chem.* 52:730-736 (1987), which is hereby incorporated by reference in its entirety), and it is possible that a similar change in solvent environment could improve the yield of Compound 7.

Regioselectivity for the reaction with ethyl nicotinate was particularly interesting; Compound 6 was the only product isolated with a mixed (4,4',6") configuration. A minor product was also produced in this reaction, but could not be isolated in sufficient quantity to permit characterization.

The obtained products 2-7 were characterized as set forth below: 2,2',2"-cyclohexane-1,3,5-triyltripyrazine (2): yellow, amorphous solid; yield: 28%; mp 122-124° C. IR (thin film from $CHCl_3$): 2922, 1576, 1523, 1472, 1406, 1248, 1152, 1058, 1016, 843, 767 cm$^{-1}$. $^1$H NMR (400 MHz, $CDCl_3$): δ 8.57 (d, J=0.8 Hz, 3H), 8.51 (t, J=1.2 Hz, 3H), 8.43 (d, J=2.0 Hz, 3H), 3.28-3.21 (m, 3H), 2.32 (d, J=10 Hz, 3H), 2.12 (q, J=10 Hz, 3H). $^{13}$C NMR (400 MHz, $CDCl_3$): δ 159.6, 144.1, 143.5, 142.9, 43.5, 37.0. HRMS: m/z calcd for $C_{18}H_{19}N_6$ (M+H)$^+$: 319.1671; found: 319.1679.

4,4',4"-cyclohexane-1,3,5-triyltripyrimidine (3): white crystalline solid; yield: 26%; mp 126-128° C. IR (thin film from $CHCl_3$): 2923, 2851, 1578, 1545, 1468, 1423, 1388, 1299, 992, 839, 679, 630 cm$^{-1}$. $^1$H NMR (400 MHz, $CDCl_3$): δ 9.14 (s, 3H), 8.66 (d, J=5.2 Hz, 3H), 7.27 (d, J=4.8 Hz, 3H), 3.16-3.08 (m, 3H), 2.33 (d, J-12.4 Hz, 3H), 2.01 (q, J=12.8 Hz, 3H). $^{13}$C NMR (400 MHz, $CDCl_3$): δ 172.1, 158.8, 157.2, 118.9, 45.0, 36.1. HRMS: m/z calcd for $C_{18}H_{19}N_6$ [M+H]$^+$: 319.1671; found: 319.1676.

4,4',4"-cyclohexane-1,3,5-triyltripyridazine (4): off white amorphous solid; yield: 5%. IR (powder): 1719 cm$^{-1}$. $^1$H NMR (400 MHz, $CDCl_3$): δ 9.23 (s, 3H), 9.20 (d, J=5.2 Hz, 3H), 7.42 (dd, J=5.2 Hz, J=2.4 Hz, 3H), 3.12 (t, J=12.2 Hz, 3H), 2.33 (d, J=12.8 Hz, 3H), 1.86 (q, J=12.4 Hz, 3H). $^{13}$C NMR (400 MHz, $CDCl_3$): δ 151.3, 151.2, 142.9, 123.9, 40.8, 37.9. HRMS: m/z calcd for $C_{18}H_{19}N_6$ (M+H)$^+$: 319.1671; found: 319.1677.

2,2',2"-cyclohexane-1,3,5-triyltri(4-pyridinecarboxylic acid, ethyl ester) (5): yellow oil; yield: 23%. IR (oil): 2981, 2927, 2907, 1683, 1599, 1561, 1472, 1445, 1393, 1108, 1067, 960, 908, 856 cm$^{-1}$. $^1$H NMR (400 MHz, $CDCl_3$): δ 8.70 (d, J=4.8 Hz, 3H), 7.84 (s, 3H), 7.70 (d, J=4.8 Hz, 3H), 4.43 (q, J=7.2 Hz, 6H), 3.31-3.28 (m, 3H), 2.37 (d, J=12.4 Hz, 3H), 2.15-2.06 (m, 3H), 1.43 (t, J=7.0 Hz, 9H). $^{13}$C NMR (400 MHz, $CDCl_3$) δ 165.8, 149.9, 138.2, 120.7, 120.5, 61.7, 46.1, 37.9, 14.2. HRMS: m/z calcd for $C_{30}H_{33}N_3O_6$ [M]$^+$: 531.2448; found: 532.2455.

4,4',6''-cyclohexane-1,3,5-triyltri(3-pyridinecarboxylic acid, ethyl ester) (6): yellow oil; yield: 16%. IR (oil): 2980, 2929, 2925, 1714, 1683, 1553, 1393, 1110, 1052, 953, 853 cm$^{-1}$. $^1$H NMR (400 MHz, CDCl$_3$): δ 9.15 (d, J=2 Hz, 1H), 9.00 (s, 2H), 8.63 (d, J=5.2 Hz, 2H), 8.21 (dd, J=8.2 Hz, J=1.8 Hz, 1H), 7.40 (d, J=5.2 Hz, 2H), 7.28 (d, J=8.4 Hz, 1H), 4.45-4.37 (m, 6H), 4.00-3.95 (m, 2H), 3.30-3.22 (m, 1H), 2.22 (d, J=12.4 Hz, 2H), 2.13 (d, J=12 Hz, 1H), 1.95 (q, J=12.4 Hz, 2H), 1.79 (q, J=12.4 Hz, 1H), 1.45-1.38 (m, 9H). $^{13}$C NMR (400 MHz, CDCl$_3$): δ 166.2, 155.6, 152.4, 151.5, 150.6, 137.6, 129.7, 125.8, 121.6, 121.5, 61.4, 46.1, 39.1, 38.7, 38.3, 14.2. HRMS: m/z calcd for C$_{30}$H$_{33}$N$_3$O$_6$ [M]$^+$: 531.2448; found: 532.2460.

2,2',2''-cyclohexane-1,3,5-triyltri(4-methylquinoline)(7): light brown powder; yield: 5%; mp=148-150° C. IR (thin film from CHCl$_3$): 3034, 1598, 1557, 1506, 1446, 1437, 1343, 1027, 856, 781, 713 cm$^{-1}$. $^1$H NMR (400 MHz, CDCl$_3$): δ 8.06 (d, J=8.4 Hz, 3H), 7.94 (d, J=8 Hz, 3H), 7.67 (t, J=7.2 Hz, 3H), 7.49 (t, J=7.2 Hz, 3H), 7.33 (s, 3H), 3.43 (t, J=12.2 Hz, 3H), 2.62 (d, J=12.4 Hz, 3H), 2.30 (q, J=12.4 Hz, 3H). $^{13}$C NMR (100.7 MHz, CDCl$_3$) δ 165.0, 147.7, 145.6, 144.4, 129.5, 128.9, 127.1, 125.4, 123.5, 120.7, 47.2, 37.8, 18.8. HRMS m/z calculated for C$_{36}$H$_{33}$N$_3$ (M+H)$^+$; calculated 508.2753. found 508.2747.

Example 2

Biphasic Variant of Tri-Directional Minisci-Type Reaction for Synthesis of 2,2',2''-cyclohexane-1,3,5-triyltripyrazine (Compound 2)

Figure 3:
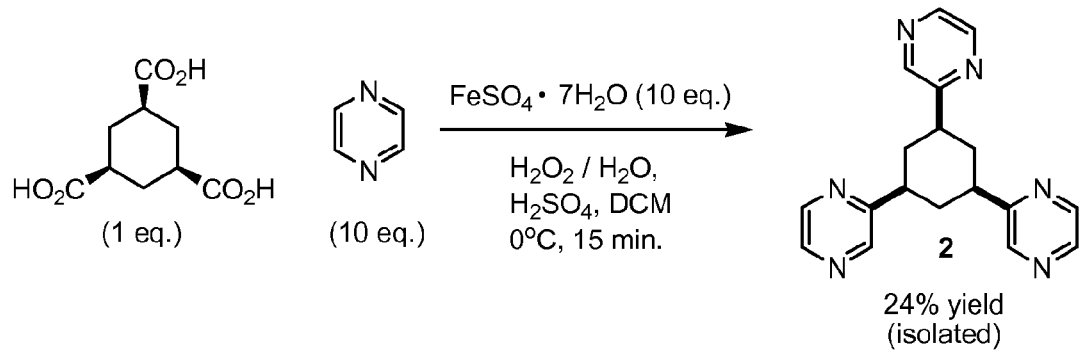
FIG. 3 shows Scheme 3, which is a tridirectional Minisci reaction performed in accordance with a second embodiment of the present invention, using a biphasic variant of the traditional Minisci reaction reported by Heinisch and Lötsch (*Angew. Chem. Int. Ed.* 24:692-693 (1985), which is hereby incorporated by reference in its entirety). Pyrazine is shown as the radical acceptor in Scheme 3, and the resulting product is Compound 2.

A biphasic variant of the traditional Minisci reaction, reported by Heinisch and Lötsch (*Angew. Chem. Int. Ed.* 24:692-693 (1985), which is hereby incorporated by reference in its entirety), was examined using pyrazine as the radical acceptor (Scheme 3; FIG. 3). Cyclohexane tricarboxylic acid (1 eq.) was reacted with pyrazine (10 eq.) and ferrous sulfate heptahydrate (10 eq.) in a hydrogen peroxide (aq.)/dichlormethane biphasic solution at 0° C. for 15 minutes. After 15 min. of stirring, the resulting mixture was poured into ice, the phases were separated, and the aqueous phase was extracted with CH$_2$Cl$_2$ (3 times, 5 ml). After drying over anhydrous Na$_2$SO$_4$, the solvent was removed in vacuo to generate a yellow oil. This oil was directly applied to silica gel and eluted with a 5% MeOH/CH$_2$Cl$_2$ solution to afford the desired compound (2) in 24% yield. Increases in reaction time did not result in an increase in yield.

Example 3

Design and Synthesis of (1s,3s,5s)-N1,N3,N5-tris(6-methylpyridin-2-yl)cyclohexane-1,3,5-tricarboxamide (Compound 11)

Compound 11 was synthesized by simple amidation reaction between cis-1,3,5-cyclohexane tricarboxylic acid and 2-amino-6-methylpyridine. Initially, the cis-1,3,5-cyclohexanetricarboxylicacid chloride was prepared by a previously described methodology (Pryor et al., *Tetrahedron.* 54:4107-4124 (1998), which is hereby incorporated by reference in its entirety). Briefly, anhydrous N,N-dimethylformamide (1.65 mmole) was added dropwise to a slurry of cis-1,3,5-cyclohexane tricarboxylic acid (2.72 mmole) and thionyl chloride (13.6 mmole) in anhydrous CH$_2$Cl$_2$. The slurry was allowed to reflux for 4 hours, and dried in vacuo to yield a yellow oil. An aliquot of the triacid chloride (0.405 mmole) was diluted to 0.1 mM in CH$_2$Cl$_2$. Then, 2-amino-6-methyl pyridine (4.05 mmole), 4-(dimethylamino)pyridine (0.202 mmole) and triethylamine (4.05 mmole) were dissolved in 10 mL anhydrous CH$_2$Cl$_2$ and added dropwise to the acid chloride. After 24 hours, the resulting yellow solution with precipitate was treated with 0.5 mL H$_2$O and dried in vacuo to yield a whitish solid. Compound 11 was purified by silica gel flash chromatography (49:1 CH$_2$Cl$_2$:CH$_3$OH) followed by preparative RP-HPLC (85:15 H$_2$O:CH$_3$CN+0.1% TFA) to a yellow oil with 51% overall yield.

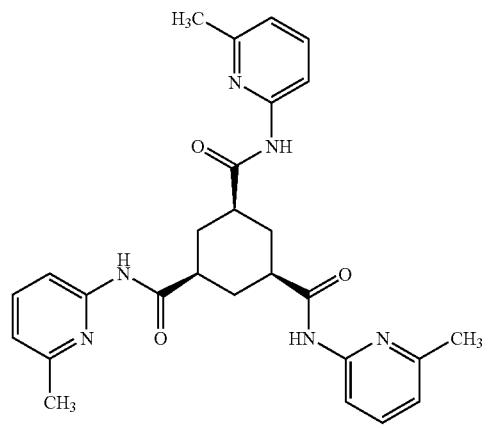

The obtained product 11 was characterized as set forth below: cis-cyclohexane-1,3,5-tricarboxylic acid tris-[(6-methyl-pyridin-2-yl)-amide] (11): IR (thin film from CDCl$_3$): 722, 798, 1153, 1196, 1431, 1636, 2867 cm$^{-1}$. $^1$H NMR (400 MHz, CDCl$_3$): as a trifluoroacetic acid salt from preparative RP-HPLC: δ 8.39 (3H, d, J=8 Hz), 8.06 (3H, t, J=8 Hz), 7.13 (3H, d, J=8 Hz), 2.97 (3H, t, J=14 Hz), 2.71 (9H, s), 2.39 (3H, d, J=12 Hz) 1.80 (3H, q, J=12). $^{13}$C NMR (100 MHz CDCl$_3$): δ 19.4, 30.1, 43.2, 114.4, 119.6, 145.8, 148.9, 150.7, 174.9. HRMS: m/z calculated for C$_{29}$H$_{34}$O$_4$ (M+H)$^+$ 487.2458, found 487.2457.

Example 4

Analysis of Compound 11 Carbohydrate Binding

Figure 5A:
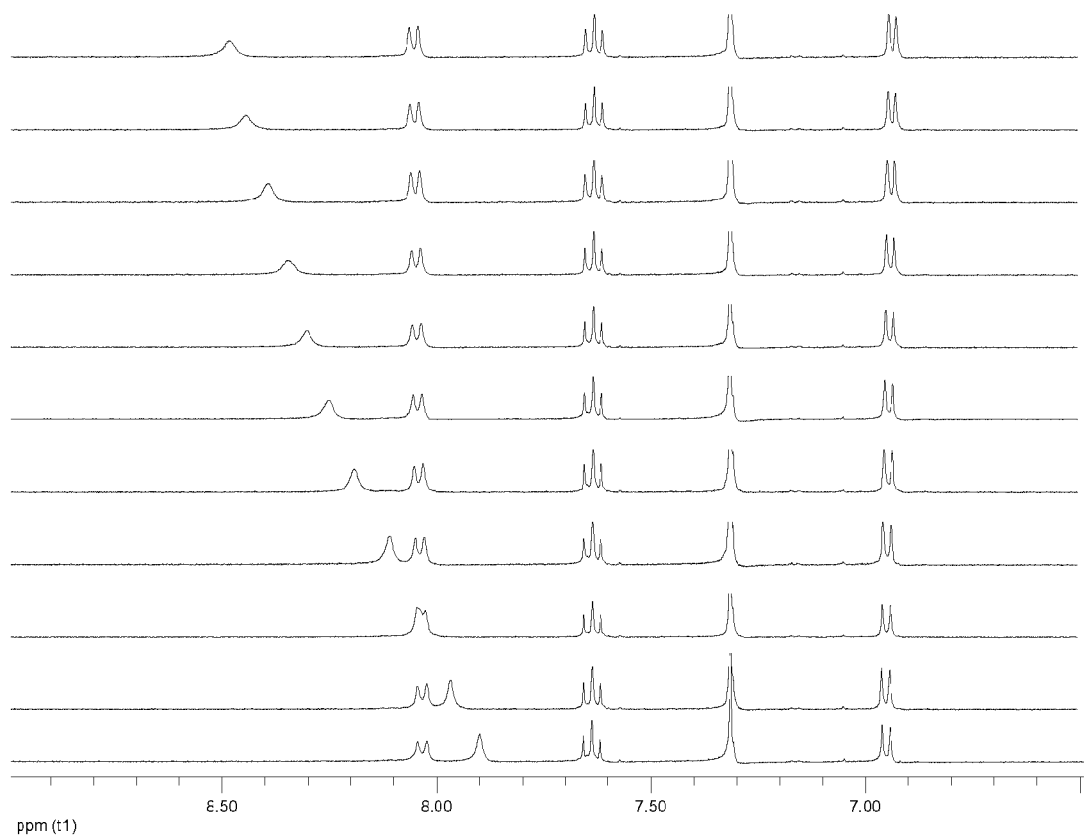
FIGS. 5A-B illustrate the titration of Compound 11 with n-octyl-β-D-glucopyranoside.

The binding affinity of Compound 11 to octyl pyranosides was tested using 1D $^1$H NMR titrations in dry and deacidified CDCl$_3$ at 298° K. The Compound 11 in fixed concentration (1 mM) was titrated with increasing amount of n-octyl-β-D-glucopyranoside and the change in the amide proton resonance of Compound 11 was monitored (FIG. 5A).

Figure 5B:
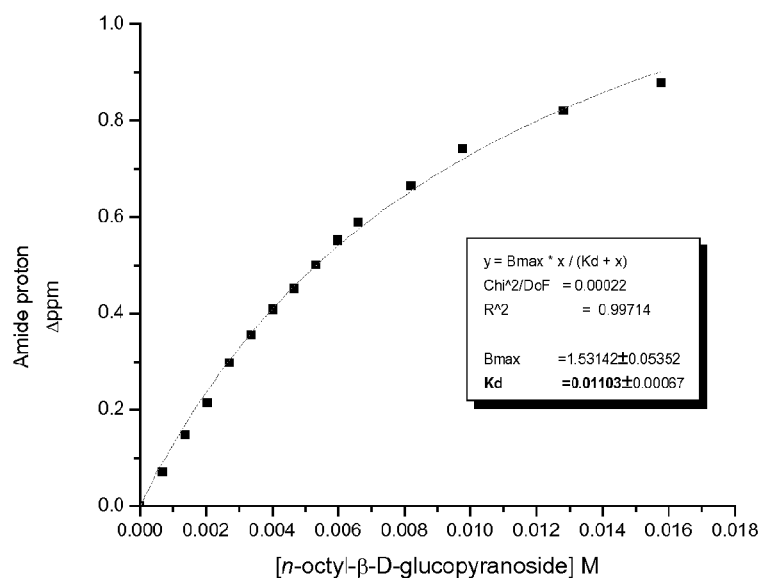

Compound 11 bound n-octyl-β-D-glucopyranoside in chloroform, as evidenced by NMR titration, but the measured affinity was relatively low ($K_a$=91 M$^{-1}$) (FIG. 5B). Conformational analysis of Compound 11 (Maestro/Batchmin 7.2; Schroedinger, Inc.) indicated that it preferentially forms an internally hydrogen-bonded conformation that is not conducive to carbohydrate binding.

Example 5

Design and Synthesis of 2,2',2''-cyclohexane-1,3,5-triyltri(4-cyanopyridinyl) (Compound 12)

Figure 6A:
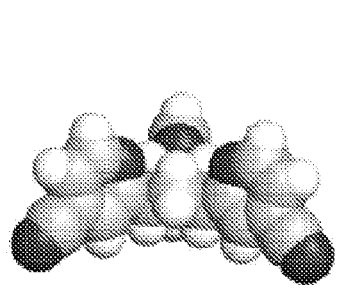
FIGS. 6A-B illustrate minimum-energy conformation (side and top views) for Compound 2.
Figure 6B:
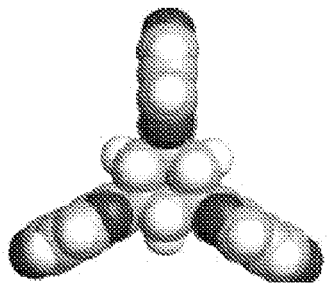
Figure 8A:
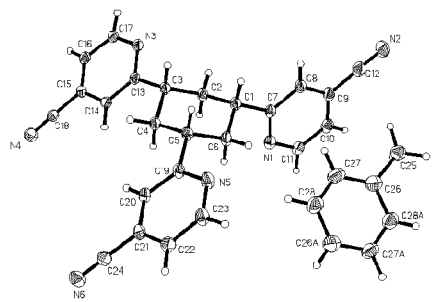
FIGS. 8A-B illustrate the Ortep plot of crystal structure of Compound 12 crystallized from toluene (8A) and methanol (8B).
Figure 8B:
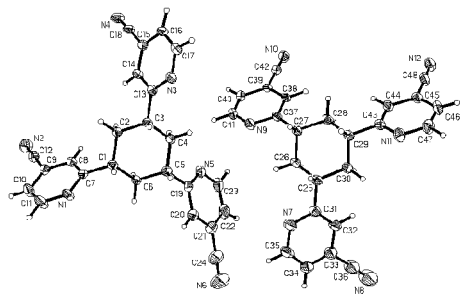

Based on the results in Example 4, it was believed that bringing the pyridine rings in closer to the central cyclohexane would improve functional group directionality as well as providing substantial receptor pre-organization. Indeed, Monte-Carlo searches and dihedral angle drives of the cyclohexane-pyridine torsional angle indicated that Compound 12 (Scheme 4, FIG. 7) would have a 2 kcal/mol preference for a conformation in which all pyridine nitrogen atoms are oriented on the same face of the molecule (FIGS. 6A-B). Synthesis of Compound 12 was readily achieved via a single-step, tri-directional Minisci reaction between cis-cyclohexane 1,3,5-tricarboxylic acid and 4-cyanopyridine (Scheme 4, FIG. 7). The procedure was essentially the same as that described in Example 1. In the process of synthesis of Compound 12, minor product Compound 14, which is the 2,2',3' regioisomer of Compound 12, was also obtained. The regioisomer served as a useful tool in the binding experiments to verify the structural and conformation requirement for binding monosaccharides. The structure of Compound 12 was confirmed by X-ray crystallography and 2-D NOE spectroscopy. The single crystal X-ray structures of Compound 12 recrystallized from either toluene (FIG. 8A) or methanol (FIG. 8B) showed that the crystal packing forces cause two of the pyridine rings to adopt a high-energy conformation, while the third adopts the minimum energy conformation predicted by the molecular mechanics calculations.

The obtained products, Compounds 12 and 14, were characterized as set forth below:

2,2',2''-cyclohexane-1,3,5-triyltri(4-cyanopyridinyl) (12): light brown solid; yield: 24%; mp=163-165° C. IR (thin film from $CHCl_3$): 2925, 2237, 1594, 1550, 1472, 1397, 1260, 842, 754 $cm^{-1}$. $^1H$ NMR (400 MHz, $CDCl_3$): δ 8.73 (d, J=4.8 Hz, 3H), 7.48 (s, 3H), 7.38 (dd, J=5 Hz, 1.4 Hz, 3H), 3.27-3.21 (m, 3H), 2.33 (d, J=12 Hz, 3H), 2.02 (q, J=12.4 Hz, 3H). $^{13}C$ NMR (100.7 MHz, $CDCl_3$) δ 165.8, 150.3, 123.2, 121.1, 116.7, 45.7, 37.4. HRMS m/z calculated for $C_{24}H_{18}N_6$ ($M^-$); 390.1600. found: 390.1601.

2,2',3'-cyclohexane-1,3,5-triyltri(4-cyanopyridinyl) (14): brown amorphous solid; yield: 4%; mp=140-142° C. IR (thin film from $CHCl_3$): 2925, 2237, 1594, 1550, 1472, 1397, 1260, 842, 754 $cm^{-1}$. $^1H$ NMR (400 MHz, $CDCl_3$): δ 8.73 (d, J=4.8 Hz, 3H), 7.48 (s, 3H), 7.38 (dd, J=5 Hz, 1.4 Hz, 3H), 3.27-3.21 (m, 3H), 2.33 (d, J=12H, 3H), 2.02 (q, J=12.4 Hz, 3H). $^{13}C$ NMR (100.7 MHz, $CDCl_3$) δ 165.8, 150.3, 123.2, 121.1, 116.7, 45.7, 37.4. HRMS m/z calculated for $C_{24}H_{18}N_6$ ($M^+$); 390.1600. found: 390.1601.

Example 6

Carbohydrate Binding Studies with Compounds 7 and 12

Figure 15:
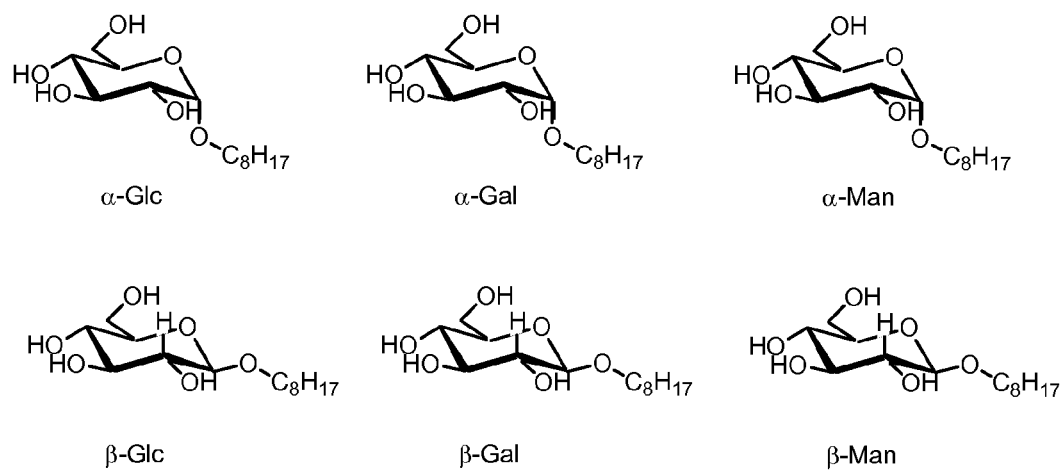
FIG. 15 shows the structures of several n-alkyl pyranosides tested. β-glc=n-octyl-β-D-glucopyranoside; α-glc=n-octyl-α-D-glucopyranoside; β-gal=n-octyl-β-D-galactopyranoside; α-gal=n-octyl-α-D-galactopyranoside; β-man=n-octyl-β-D-mannopyranoside; α-man=n-octyl-α-D-mannopyranoside.

The binding affinity of Compound 12 towards a set of octylglycosides (FIG. 15) was measured using $^1H$ NMR titrations in $CDCl_3$ and UV titrations in chloroform and methanol. Since Compound 7 exhibited intrinsic fluorescence properties, the binding studies for Compound 7 with different monosaccharides were performed using fluorescence titrations in methanol.

Figure 9A:
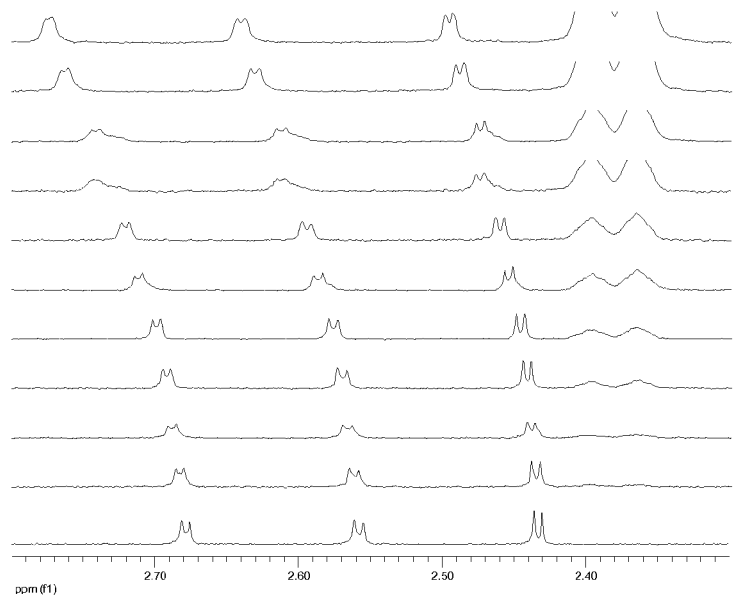
FIGS. 9A-B illustrate 1D $^1$H NMR titration of Compound 12 into n-octyl-β-D-glucopyranoside (1.09 mM).
Figure 9B:
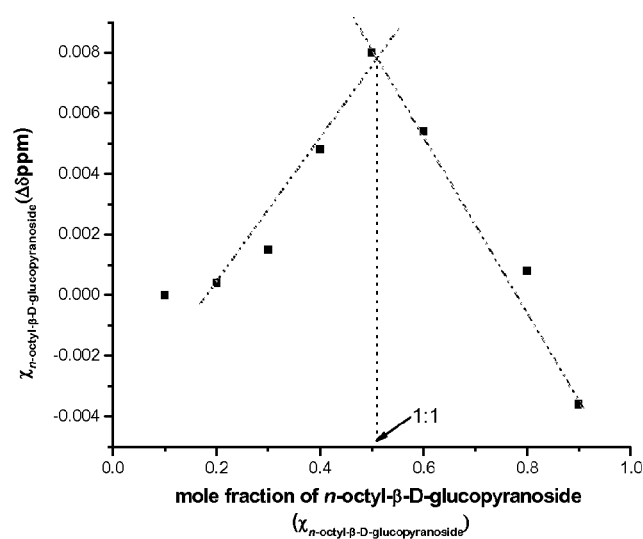

A reverse titration format (receptor into the sugar) was employed for estimating binding by $^1H$ NMR titrations in order to avoid the complications caused due to micelles formation by octylglycosides at higher concentrations (Vacca et al., *J. Am. Chem. Soc.* 126:16456-16465 (2004), which is hereby incorporated by reference in its entirety). After verifying that Compound 12 showed no concentration-dependent changes in its NMR spectrum, it was titrated into a solution of octyl glucopyranosides. Receptor-dependent changes in carbohydrate hydroxyl chemical shifts indicating binding were clearly visible (FIG. 9A). Importantly, no chemical shift changes were observed in an analogous titration of 4-cyanopyridine into n-octyl-β-D-glucopyranoside. This result confirms that binding requires the full structure of the receptor, and is not due to nonspecific interactions between the alkyl glucosides and 4-cyanopyridine. Job plot analysis (as modified for NMR) (Fokkens et al., *Chem. Eur. J.* 11:477-494 (2005), which is hereby incorporated by reference in its entirety) verified a 1:1 association between Compound 12 and n-octyl-β-D-glucopyranoside (FIG. 9B).

Example 7

Ultraviolet Titration Studies with Compound 12

To derive quantitative binding information, UV-Vis titrations were performed. The receptor at fixed concentration was titrated with the octylglycosides in dry and deacidified chloroform or methanol (298° K). Each titration was performed in duplicate to verify results.

Figure 10:
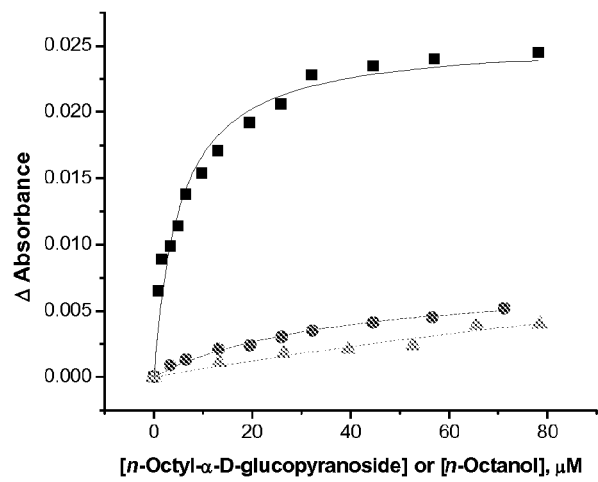
FIG. 10 is a plot of the UV-Vis titration of n-octyl-α-D-glucopyranoside into Compound 12 (squares) or Compound 14 (circles). Titration of n-octanol into Compound 12 (triangles) is shown as a control.

An increase in the intensity of absorbance of Compound 12 was observed upon increasing concentration of monosaccharides. Compound 12 showed highest binding affinity for n-octyl-α-D-glucopyranoside ($K_n$=183,000±4,200 $M^{-1}$) among the set of monosaccharides tested (FIG. 10; Table 1 below). This is the highest binding affinity reported so far for any artificial receptor towards n-octyl-α-D-glucopyranoside. Also observed was a substantial selectivity for glucosides over other sugars: while the n-octyl-β-D-galactopyranoside binds with roughly half the affinity of the β-D-glucopyranoside, n-octyl-β-D-mannopyranoside did not reach saturation up to the limit of the titration (Table 1).

TABLE 1

| UV-Vis titration of selected n-octyl monosaccharides with Compound 12 | | |
|---|---|---|
| n-octyl pyranoside | $K_a$ in chloroform ($M^{-1}$) | $K_a$ in methanol ($M^{-1}$) |
| β-D-gluco | 25,000 ± 600 | 11,100 ± 600 |
| α-D-gluco | 183,000 ± 4,200 | 52,000 ± 2,700 |
| β-D-galacto | 9,800 ± 100 | 7,200 ± 1,700 |
| α-D-galacto | 17,600 ± 100 | 9,200 ± 1,100 |
| β-D-manno | (not saturable) | (not saturable) |
| α-D-manno | 6,700 ± 700 | >1,200 |
| Octanol (control) | (no binding) | not determined |

No binding was observed between Compound 12 and octanol indicating that there is no non-specific interaction involved between 12 and the octyl chain of glycopyranosides. Likewise, compound 14, obtained as a minor product in the synthesis of 12, showed no affinity for n-octyl-α-D-glucopyranoside, thus emphasizing the importance of structural features in the binding process. Combined with the NMR titration data described above, these data demonstrate that the ability of 12 to bind alkyl pyranosides in chloroform is highly selective, and that proper positioning of the three pyridine rings is an absolute requirement for high affinity.

Although Compound 12 shows excellent binding affinity and selectivity in chloroform, it was interesting to find out its capability to function in polar protic solvents, where the competition from the solvent molecules is usually high. Hence, binding in methanol was also examined. UV titrations again demonstrated that Compound 12 binds alkyl pyranosides with high affinity and selectivity (Table 1, right column). While the affinities are slightly reduced relative to those measured in chloroform (as would be expected because of increased competition from solvent binding), the rank order of affinities is maintained. This suggests that the mode of binding is not altered to any great extent by the change in solvent.

Example 8

Fluorescence Titration Studies with Compounds 7 and 12

Figure 11A:
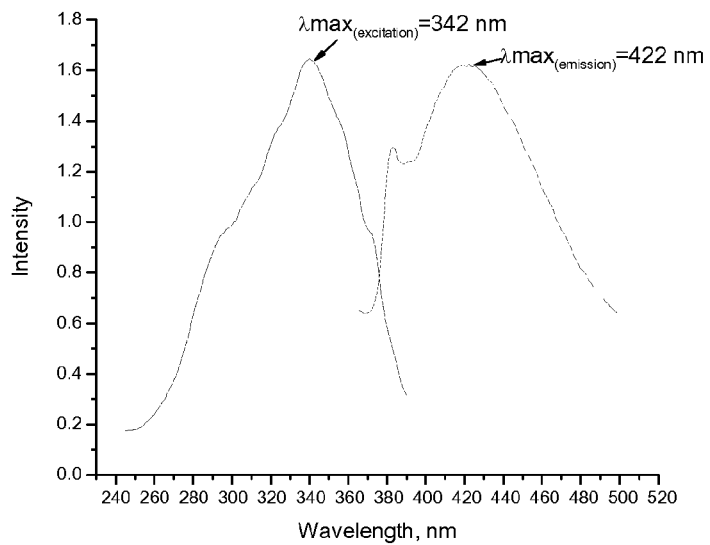
FIGS. 11A-C illustrate the analysis of Compound 7.
Figure 11B:
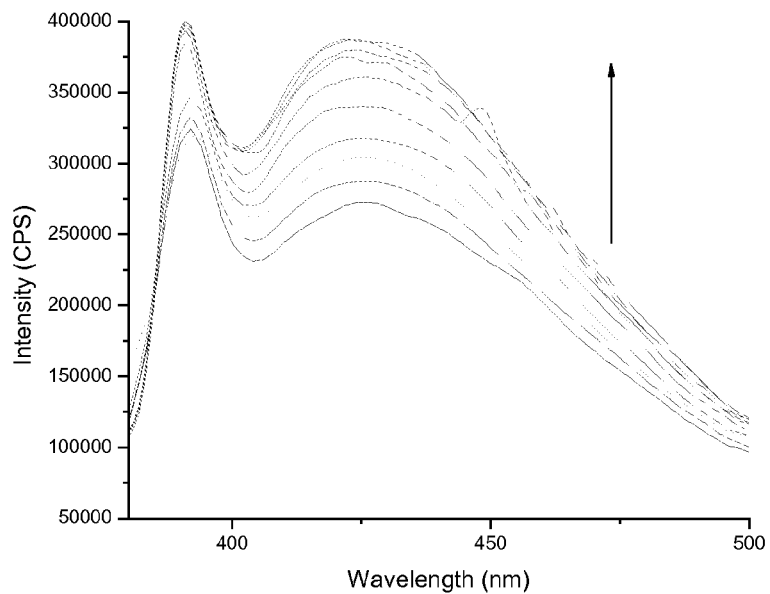
Figure 11C:
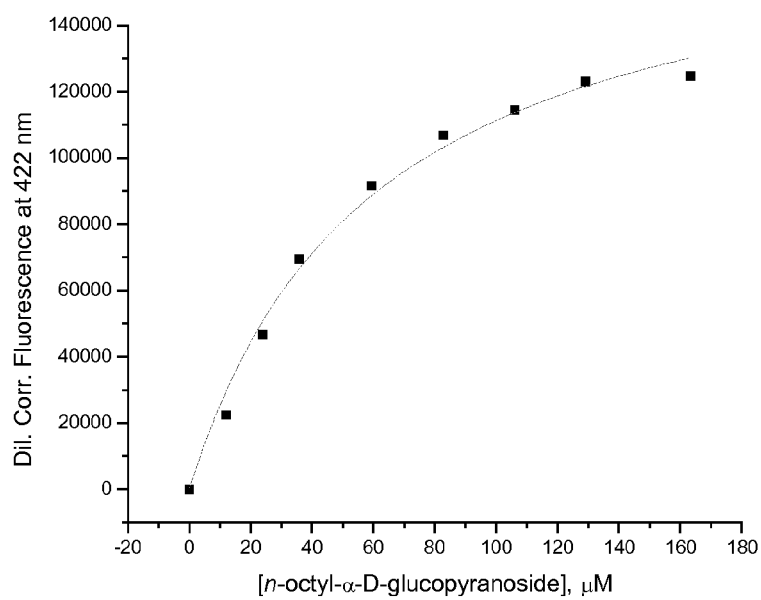

Compound 7 was found to exhibit fluorescence at 422 nm when excited with a wavelength of 350 nm (FIGS. 11A-C). The same titration protocol employed in Example 7 was also employed in this Example (methanol at 298° K; duplicate titrations).

Fluorescence titrations of 7 with the set of octylglycosides (FIG. 15) in methanol were performed to study the effect of substitution of 4-methylquinoline instead of 4-cyanopyridine on the binding affinity and selectivity of Compound 12. Receptor 7 showed slightly lower binding affinity for n-octyl-α-D-glucopyranoside in methanol ($K_a = 14,900 \pm 1700$ $M^{-1}$) as compared to Compound 12 (compare Tables 1, right column, and 2). Interestingly, Compound 7 binds monosaccharides with a selectivity pattern virtually identical to that displayed by Compound 12 (see Tables 1, right column, and 2). The stoichiometry of binding between Compound 7 and n-octyl-α-D-glucopyranoside was determined by Job plot to be 1:1 (FIG. 12).

TABLE 2

Fluorescence Titrations of selected n-octyl monosaccharides with Compound 7

| n-octyl pyranoside | $K_a$ in methanol ($M^{-1}$) |
|---|---|
| β-D-gluco | 9,200 ± 600 |
| α-D-gluco | 14,900 ± 1700 |
| β-D-galacto | 3,200 ± 80 |
| α-D-galacto | 6,600 ± 200 |
| β-D-manno | >400 |
| α-D-manno | 2600 ± 200 |
| octanol (control) | (no binding) |

Example 9

1-D Difference NOE and 2-D NOE Studies on Compound 12

Figure 14:
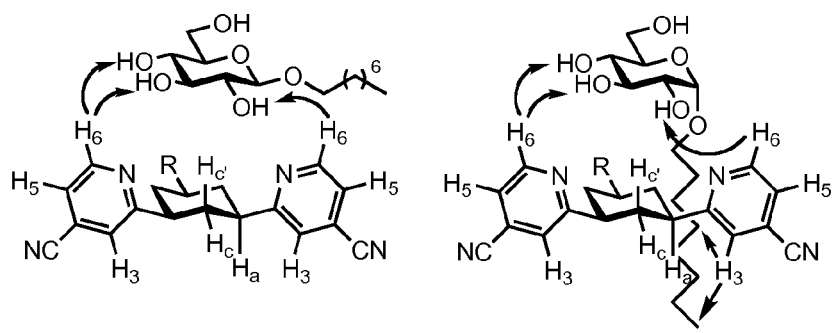
FIG. 14 is a summary of NOE interactions observed between Compound 12 and n-octyl-α-D-glucopyranoside (left) or n-octyl-β-D-glucopyranoside (right) in CDCl₃.

One-dimensional difference NOE experiments on Compound 12 in the presence of n-octyl-pyranosides in CDCl$_3$ were used to derive a preliminary model for binding. Selective irradiation of the C-6 aromatic proton of Compound 12 in the presence of n-octyl-β-D-glucopyranoside showed enhancement of the 2-, 3- and 4-OH protons of the sugar (FIGS. 13A-B). This suggests that the sugar —OH protons are possibly H-bonded to the pyridine nitrogens of Compound 12 and, hence, in the NOE distance range of the C-6 aromatic protons. The 2-D NOE studies in CDCl$_3$ also revealed some crucial intermolecular NOE contacts between the receptor and octyl glucosides. The key NOE contacts (summarized in FIG. 14) indicate that both the α- and β-octyl glucosides bind with a similar orientation. It is possible that hydrophobic interactions between the receptor and octyl chain may contribute to the enhanced affinity for the α-anomer. In contrast, the decrease in affinity for galacto- and mannopyranosides is likely due to the loss of hydrogen bonding opportunities.

Discussion of Examples

The results presented in the preceding examples demonstrate that the single-step Minisci reaction is suitable for the preparation of a broad array of tripodal carbohydrate receptors using a cis-1,3,5-trisubstituted cyclohexane core structural element. Importantly, Compound 12 shows the highest affinity recorded to date for noncovalent recognition of monosaccharides in protic solvent (methanol), and also has significant selectivity in both chloroform and methanol. This confirms that this compound should be useful in other protic and non-protic organic solvents. Although the binding affinities shown by Compound 7 towards different monosaccharides are slightly reduced from those of Compound 12, Compound 7 has an advantage in that it exhibits fluorescence and hence the detection of binding is easier. Compound 12 should be suitable for simple derivatization via several methods, including hydrolysis of the nitrile groups on each aromatic ring.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A compound according to formula (I)

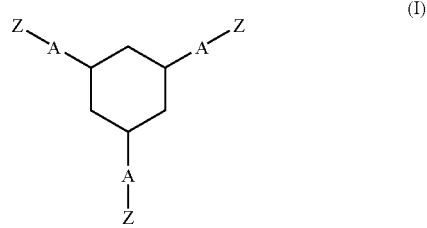

wherein,
each Z is the same and is a substituted or unsubstituted N-heteroaromatic single- or multiple-ring selected from the group of pyridine, pyrazine, pyrimidine, pyridazine, imidazole, pyrrole, oxazole, isooxazole, triazine, thiazole, indazole, purine, quinoline, isoquinoline, quinoxaline, quinazoline, cinnoline, benzoxazole, benzisooxazole, and benzothiazole,
each A is a direct bond between the cyclohexane ring and Z, and
the N-heteroaromatic ring is attached directly to the cyclohexane ring through a carbon atom that is in adjacent position to a nitrogen heteroatom in the N-heteroaromatic ring.

2. The compound according to claim 1 wherein the compound is a substantially pure cis stereoisomer.

3. The compound according to claim 1, wherein Z is an N-heteroaromatic single-ring.

4. The compound according to claim 1, wherein Z is an N-heteroaromatic multiple-ring.

5. The compound according to claim 1 wherein Z is selected from the group consisting of pyridine, pyrazine, pyrimidine, pyridazine, imidazole, pyrrole, oxazole, isooxazole, triazine, and thiazole comprising one to four substituents independently selected from the group consisting of —COO—R₁ where R₁ for each substituent is independently —H or a C1 to C18 hydrocarbon that is saturated or unsaturated;

-(hydrocarbon)$_n$-R₂ where for each substituent the hydrocarbon is saturated or unsaturated, n is an integer from 0 to 20, and R₂ is independently —OH, —CH₃, or —COOH; and

—CN.

6. The compound according to claim 1, wherein Z is selected from the group consisting of indazole, purine, quinoline, isoquinoline, quinoxaline, quinazoline, cinnoline, benzoxazole, benzisooxazole, and benzothiazole comprising one to six substituents independently selected from the group consisting of —COO—R₁ where R₁ for each substituent is independently —H or a C1 to C18 hydrocarbon that is saturated or unsaturated;

-(hydrocarbon)$_n$-R₂ where for each substituent the hydrocarbon is saturated or unsaturated, n is an integer from 0 to 20, and R₂ is independently —OH, —CH₃, or —COOH; and

—CN.

7. The compound according to claim 1 wherein the compound is 1,3,5-tris-pyrazin-2-yl cyclohexane;
1,3,5-tris-pyrimidin-2-yl cyclohexane;
1,3,5-tris[1,3,5-triazin-2-yl]cyclohexane;
1,3,5-tris-pyridazin-3-yl cyclohexane;
1,3,5-tris-imidazol-2-yl cyclohexane;
1,3,5-tris-pyridin-2-yl cyclohexane;
1,3,5-tris-(4-cyano)pyridin-2-yl cyclohexane;
1,3,5-tris-(4-carboxylic acid)pyridin-2-yl cyclohexane;
1,3,5-tris-(4-ethyl ester)pyridin-2-yl cyclohexane;
1,3,5-tris-(4-ethyl-2-acetamido)pyridin-2-yl cyclohexane;
1,3,5-tris-(4-methyl)pyridin-2-yl cyclohexane;
1,3,5-tris-(4-methoxy)pyridin-2-yl cyclohexane;
1,3,5-tris-(4-amino)pyridin-2-yl cyclohexane;
1,3,5-tris-(4-cyano-6-(2-hydroxyethylamino))pyridin-2-yl cyclohexane;
1,3,5-tris-(4-cyano-6-(3-hydroxypropylamino))pyridin-2-yl cyclohexane;
1,3,5-tris-(4-cyano-6-(N-(pyridin-2-ylmethyl)amino)-pyridin-2-yl cyclohexane;
1,3,5-tris-(3,5-methoxy-4-cyano-6-(2-hydroxyethylamino))pyridin-2-yl cyclohexane;
1,3,5-tris-(3,5-methoxy-4-cyano-6-(3-hydroxypropylamino))pyridin-2-yl cyclohexane;
1,3,5-tris-(3,5-methoxy-4-cyano-6-(N-(pyridin-2-ylmethyl)amino)-pyridin-2-yl cyclohexane;
1,3,5-tris-(4-carboxylic acid-6-(2-hydroxyethylamino))pyridin-2-yl cyclohexane;
1,3,5-tris-(4-carboxylic acid-6-(3-hydroxypropylamino))pyridin-2-yl cyclohexane;
1,3,5-tris-(4-carboxylic acid-6-(N-(pyridin-2-ylmethyl)amino)-pyridin-2-yl cyclohexane;
1,3,5-tris-(4-methyl-6-(2-hydroxyethylamino))pyridin-2-yl cyclohexane;
1,3,5-tris-(4-methyl-6-(3-hydroxypropylamino))pyridin-2-yl cyclohexane;
1,3,5-tris-(4-methyl-6-(N-(pyridin-2-ylmethyl)amino)-pyridin-2-yl cyclohexane;
1,3,5-tris-(4-methoxy-6-(2-hydroxyethylamino))pyridin-2-yl cyclohexane;
1,3,5-tris-(4-methoxy-6-(3-hydroxypropylamino))pyridin-2-yl cyclohexane;
1,3,5-tris-(4-methoxy-6-(N-(pyridin-2-ylmethyl)amino)-pyridin-2-yl cyclohexane;
1,3,5-tris-(4-amino-6-(2-hydroxyethylamino))pyridin-2-yl cyclohexane;
1,3,5-tris-(4-amino-6-(3-hydroxypropylamino))pyridin-2-yl cyclohexane; or
1,3,5-tris-(4-amino-6-(N-(pyridin-2-ylmethyl)amino)-pyridin-2-yl cyclohexane.

8. A method of making a compound according to formula (I) of claim 1, said method comprising:

reacting, via tri-directional Minisci reaction, 1,3,5-tricarboxylic acid cyclohexane and a substituted or unsubstituted N-heteroaromatic compound (H—Z) where Z is defined as in claim 1.

9. The method according to claim 8 wherein the 1,3,5-tricarboxylic acid cyclohexane is a substantially pure cis stereoisomer.

10. The method according to claim 8 wherein said tri-directional Minisci reaction comprises a single-step, tri-directional Minisci reaction between 1,3,5-tricarboxylic acid cyclohexane and H—Z, and the one or more substituents, when present, is selected from the group of —COO—R₁ where R₁ for each substituent is independently —H or a C1 to C18 hydrocarbon that is saturated or unsaturated, and

—CN.

11. A compound according to formula (II):

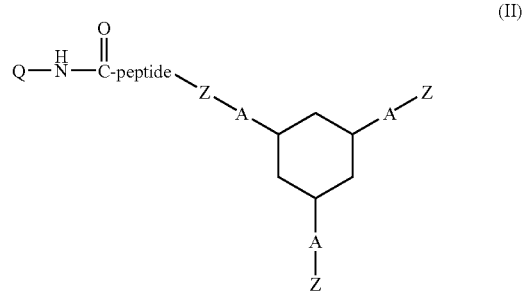

wherein, each Z is the same and is a substituted or unsubstituted N-heteroaromatic single or multiple-ring;

each A is the same, and is a direct bond between the cyclohexane ring and Z;

the peptide comprises 2 to 5 amino acids, and at least one of the amino acids comprises a thiol group or an unsaturated hydrocarbon sidechain; and Q is H.

12. A method of detecting the presence of a carbohydrate in a sample comprising:

providing a sample containing a carbohydrate of interest;

exposing the sample to a compound according to claim 1; and determining whether the compound binds to the carbohydrate of interest.

13. A compound according to formula (I)

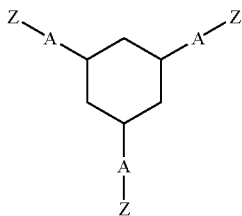

wherein,
each A is a direct bond between the cyclohexane ring and Z;
each Z is the same and is a substituted or unsubstituted N-heteroaromatic single- or multiple-ring selected from the group of pyridine, pyrazine, pyrimidine, pyridazine, imidazole, pyrrole, oxazole, isooxazole, triazine, thiazole, indazole, purine, quinoline, isoquinoline, quinoxaline, quinazoline, cinnoline, benzoxazole, benzisooxazole, and benzothiazole, comprising one or more substituents independently selected from the group consisting of
—COO—$R_1$ where $R_1$ for each substituent is independently —H or a C1 to C18 hydrocarbon that is saturated or unsaturated,
-(hydrocarbon)$_n$-$R_2$ where for each substituent the hydrocarbon is saturated or unsaturated, n is an integer from 0 to 20, and $R_2$ is independently —OH, —$CH_3$, or —COOH, and
—CN; and
the N-heteroaromatic ring is attached directly to the cyclohexane ring through a carbon atom that is in adjacent position to a nitrogen heteroatom in the N-heteroaromatic ring.

* * * * *